United States Patent [19]

Hansen

[11] Patent Number: 4,618,822

[45] Date of Patent: Oct. 21, 1986

[54] DISPLACEMENT SENSING DEVICE UTILIZING ADJUSTABLE TUNED CIRCUIT

[75] Inventor: Per K. Hansen, Burlington, Vt.

[73] Assignee: Position Orientation Systems, Ltd., Burlington, Vt.

[21] Appl. No.: 601,681

[22] Filed: Apr. 18, 1984

[51] Int. Cl.$^4$ ............................................... G01B 7/14
[52] U.S. Cl. ................................... 324/207; 128/782; 324/236; 340/572
[58] Field of Search ............... 324/207, 208, 232, 236; 336/30, 130; 246/249; 340/551, 572, 870.36; 128/631, 774, 782, 903

[56] References Cited

U.S. PATENT DOCUMENTS

| | | | |
|---|---|---|---|
| 3,020,639 | 2/1962 | Karpovich et al. | 128/782 |
| 3,253,588 | 5/1966 | Yuilleumier et al. | 128/734 X |
| 4,284,961 | 8/1981 | Landau | 324/208 X |
| 4,333,072 | 6/1982 | Beigel | 340/572 X |

*Primary Examiner*—Reinhard J. Eisenzopf
*Assistant Examiner*—Robert W. Mueller
*Attorney, Agent, or Firm*—Sherman and Shalloway

[57] ABSTRACT

Disclosed are two embodiments of displacement sensing devices utilizing adjustable tuned circuits. In a first embodiment, a sensor comprising a capacitor and an adjustable coil connected together is attached to two relatively movable objects; the relative displacement of which is to be measured. An electrical circuit is provided which includes an oscillator which may be swept through a predetermined range of frequencies so as to variably excite a source coil. As the oscillator is swept through these frequencies, a comparator compares the voltage output of the oscillator with the voltage output of the source coil. When the frequency of the oscillator is equal to the resonant frequency of the sensor circuit at its particular coil displacement, a voltage drop across the source coil will be sensed by the electrical circuitry and from this information, the circuitry may calculate the actual displacement of the two objects with respect to one another. In a second embodiment of the present invention, the same sensor is used and the electrical circuitry includes an oscillator which places a voltage across a source coil while the oscillator frequency is swept between two predetermined extremes. A separate detector coil is provided in the electrical circuitry and this detector coil senses phase changes caused by the effect of the source coil frquency upon the sensor circuitry. A phase-to-voltage converter converts the phase of the detector coil to a voltage which is indicative of the displacement of the objects with respect to one another.

18 Claims, 16 Drawing Figures

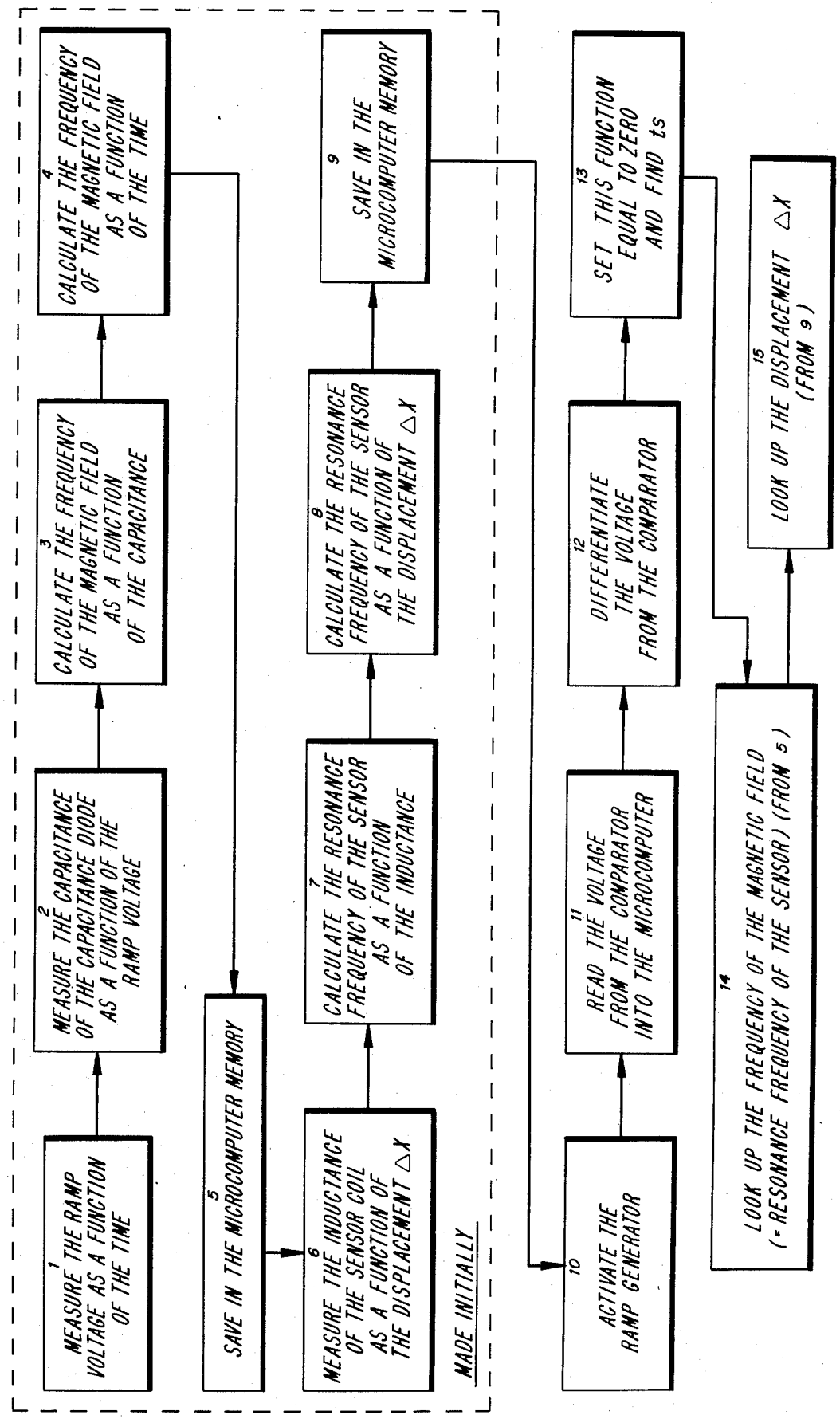

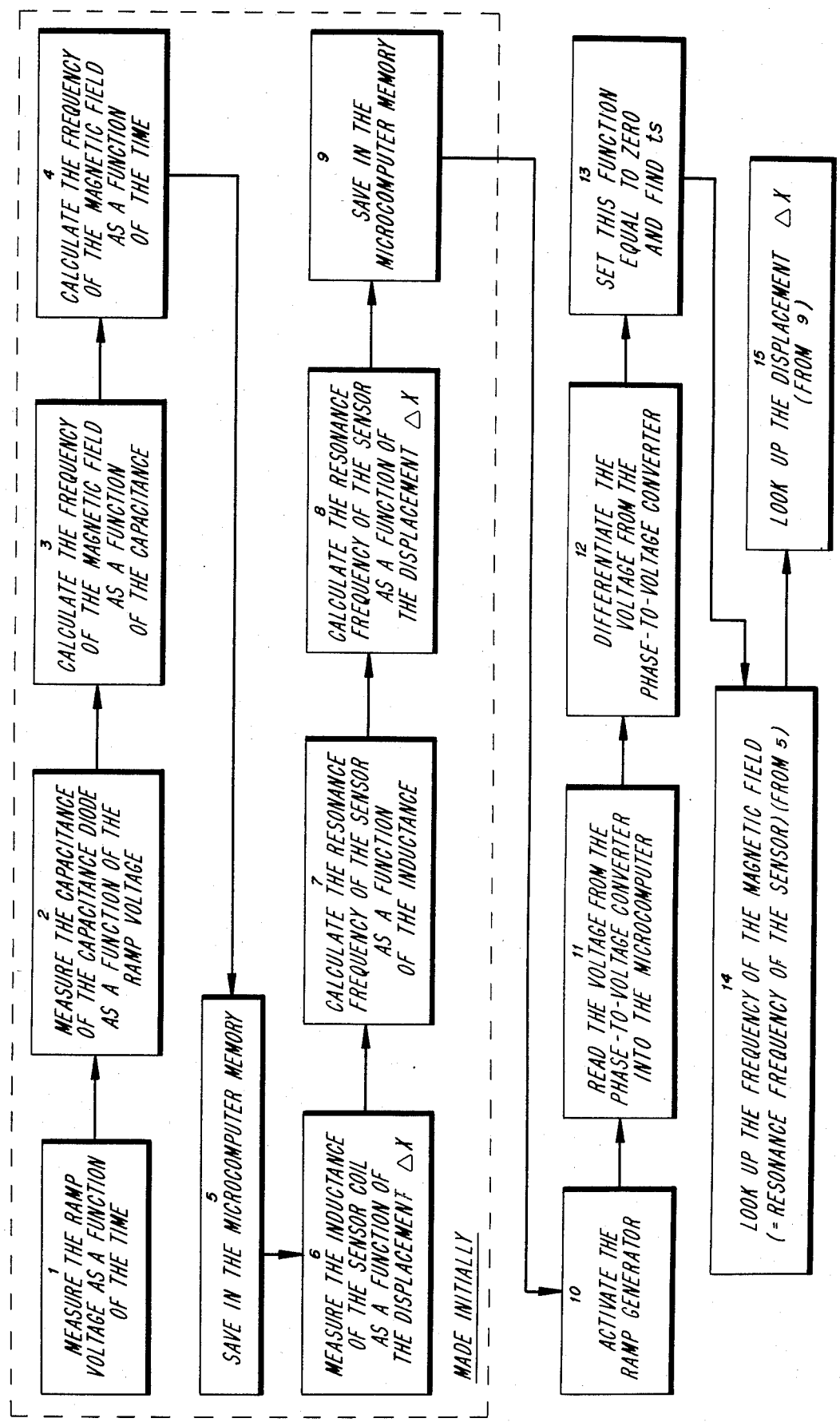

DISPLACEMENT SENSING DEVICE UTILIZING ADJUSTABLE TUNED CIRCUIT

BACKGROUND OF THE INVENTION

This invention relates to embodiments of displacement sensing devices utilizing adjustable tuned circuitry. In the prior art, the use of tuned circuits is well known, however, applicant is aware of no prior art which utilizes the concept of the tuned circuit in the manner with which tuned circuits are used in the present invention. The following prior art is known to applicant:

U.S. Pat. No. 2,495,157 to Browne, Jr. discloses an electro-magnetic device including an armature having lateral projections which extend adjacent a core having primary and secondary windings. A voltage is connected to the primary winding and the voltage induced in the secondary winding is dependent upon the position of the armature with respect to the secondary winding. An indicator is provided to indicate the induced voltage. This invention is vastly different from the inventions disclosed herein mainly because (1) the source and the sensor are connected to the same core and as such are not separated as is the case in the present invention, (2) there is no use in this patent of a passive resonant circuit as is used in the present invention, (3) there is no use of frequency sweeping to detect the resonance, and (4) the patent only discloses the measurement of the displacement of one magnetic core whereas the systems of the present invention may measure the displacement of several ferrite rods in their respective resonant circuits simultaneously. A further distinction lies in the fact that the indication means of the present invention comprises a computerized readout whereas in the patented invention a simple indicator is used.

U.S. Pat. No. 3,420,222 to Noe, et al. discloses a device designed to detect physiological movement. As shown in FIG. 1, a primary coil has a voltage induced therein by an oscillator (FIG. 3). Any movement of the core located within the coil caused by movements of the legs connected to the core induces voltages in the coils indicative of the position of the core. This device is different from the inventions disclosed herein for the same reasons noted above with respect to U.S. Pat. No. 2,495,157. It is further noted that Noe, et al comprises a balanced bridge type arrangement which is different from the teachings of the present invention.

U.S. Pat. No. 3,735,244 to Gamtau, et al. discloses a device wherein a coil forms a part of a tuned circuit with a core extending through the coil. An oscillator is utilized to provide voltage to the coil and as the position of the core within the coil changes, the amplitude of the oscillations change as an indication thereof. The teachings of this patent are significantly different from the teachings of the present invention in that (1) the source and the sensor are not separated as is the case in the present invention, (2) no passive resonant circuit is used, (3) no frequency sweep is used, (4) the patented system is only usable to measure the displacement of one magnetic core whereas the systems of the present invention may measure the displacement of several ferrite rods in their respective passive resonant circuits simultaneously, and (5) the computerized readout and calculation aspect of the present invention are not taught or suggested in this patent.

U.S. Pat. No. 4,075,553 to Bouverot, et al. discloses a device which utilizes the concept of "phase change" to determine the presence of a metallic object. The device includes a transmitter coil and receiver coils. When a metallic object is present, a phase difference occurs which is sensed to the use of a phase comparer. This patent is believed to be only generally related to the inventions disclosed herein since the invention disclosed therein measures only the presence of a metallic object and not its exact position. Other differences like those described hereinabove are also present between the teachings of this patent and those of the present invention.

U.S. Pat. No. 4,112,365 to Larson, et al. is believed to be similar to the above discussed U.S. Pat. No. 4,075,553 to Bouverot, et al. with the further provision of utilizing phase shift to determine the position and/or velocity of an object. The effective impedance of a sensing coil changes due to the movement of metallic material, which causes the phase of voltage over the coil to shift. This phase is indicative of the position of the object and the rate of the phase shift is indicative of the speed of the object. Significantly, in this patent, the source and the sensor are not separated which is vastly different from the teachings of the present invention wherein the source and sensor comprise individual components separated from one another by significant distances.

U.S. Pat. No. 4,134,065 to Bauer, et al. discloses a system wherein the position of a core with respect to a coil system is indicated by the phase shift in an oscillating voltage. In this invention, the phase shift is determined and thereby the core position is calculated. This patent is believed to be similar to U.S. Pat. No. 2,495,157 in that the displacement of a magnetic core is directly converted into phase information. As such, the differences between this patent and the present invention are similar to the differences between U.S. Pat. No. 2,495,157 and the present invention.

U.S. Pat. No. 4,263,551 to Gregory, et al. discloses a system wherein the presence of a metallic object between two coils is detected through a detector sensitive to phase change. This invention is believed to be different from the present invention in that (1) the source and the sensor are not separated, (2) the source and the sensor are wound around the same magnetic core, (3) only the presence of the conductive object is measured and not the exact position thereof, and (4) no passive resonant circuit or frequency sweep are used.

U.S. Pat. No. 4,350,954 to Seilly discloses an inductive type displacement transducer which includes a core within windings with the inductance thereof being dependent upon the extent to which the core is within the windings. This system is similar to that which is disclosed in U.S. Pat. No. 3,735,244 differing mainly therefrom in that the sensor coil is wound somewhat differently and a reference coil is used. The teachings of this patent differ from the teachings of the present invention for the same reasons discussed hereinabove with respect to U.S. Pat. No. 3,735,244.

U.S. Pat. No. 3,891,918 to Ellis discloses a linear displacement transducer utilizing an oscillator wherein the oscillator includes a coil with a moveable magnetic core as a part thereof. The movement of the magnetic core changes the inductance of the coil and thereby the frequency of the oscillator. The frequency of the oscillator is measured and is indicative of the displacement of the magnetic core with respect to the coil. Again, this patent differs from the teachings of the present invention for the same reasons discussed hereinabove with respect to U.S. Pat. No. 3,735,244. Mainly, it is noted that in Ellis, the source and the sensor are interconnected, no passive resonant circuit is used, there is no use of frequency sweep to determine positioning and there is no computerized calculation and readout in this system.

The following patents are also known to applicant but are believed to be only generally related to the teachings of the present invention: U.S. Pat. Nos. 2,630,559, 2,949,910, 3,020,527, 3,043,309, 3,253,588, 3,777,255, 3,782,188, 3,911,899, 3,990,065, 4,026,276, 4,107,604, 4,206,769, 4,207,520, 4,229,696, 4,168,496, 4,252,129, 4,277,828.

SUMMARY OF THE INVENTION

The present invention overcomes the deficiencies and shortcomings of the prior art as discussed hereinabove by providing two embodiments of displacement sensing devices utilizing adjustable tuned circuits. In a first embodiment of the present invention, the following features are included:

(A) a position displacement sensor is provided which includes one end including a coil connected to a capacitor. This first end further includes means enabling the first end to be attached to a first object. The position displacement sensor further includes a second end including a ferrite rod adjustably fitting within the above described coil and further including attachment means to attach this second end to a second object the position of which is to be determined with respect to the first object.

(B) the system further includes electrical circuitry which is sensitive to movements of the ferrite rod within the coil in the position displacement sensor to thereby measure the relative position of the first object with respect to the second object. This electrical circuitry includes a source coil connected to an oscillator which oscillator may place a voltage across the source coil while changing the frequency of this voltage in a controlled variable manner.

(C) the electrical circuitry further includes a comparator which is connected therein so as to enable a comparison of the voltage output of the oscillator with the voltage output of the source coil.

(D) the position displacement sensor comprises a tuned circuit having differing resonant frequencies for differing positions of the ferrite rod within the coil thereof. It is the nature of the system that when the source coil voltage output is at the resonant frequency of the position displacement sensor, the source coil will exhibit a voltage drop. Thus, whenever a voltage drop occurs, the comparator will output the difference between the oscillator voltage and the source coil voltage to a microcomputer which is programmed to calculate the position of the ferrite rod with respect to the coil of the position displacement sensor based upon this difference between the oscillator voltage and the source coil voltage.

(E) the above mentioned microcomputer is further programmed to control the sweeping of frequencies by the oscillator as well as to calculate the position of the ferrite rod. Of great importance is the fact that the position displacement sensor is totally separated from the electrical circuitry of the present invention and only causes a voltage drop across the source coil through resonance not through any positive electrical connection.

The second embodiment of the present invention also overcomes the deficiencies above noted in the prior art by providing the following combination of features:

(A) the position displacement sensor utilized in this embodiment is identical to that which is utilized in the above described embodiment.

(B) in this embodiment, a source coil is utilized which is similar to the source coil utilized in the above describe embodiment with an oscillator connected to the source coil to provide a variable frequency voltage thereacross so as to enable determination of the resonant frequency of the position displacement sensor.

(C) a separate detector coil is connected into the electrical circuitry of this embodiment and a phase-to-voltage converter is connected to the detector coil to convert any changes in the phase of the voltage across the detector coil into a voltage usable by the computer included in the electrical circuitry. It has been found that phase changes in the voltage induced across the detector coil are indicative of the position of the ferrite rod of the position displacement sensor with respect to its coil.

(D) the computer of the system is programmed with information relating to voltages outputted by the phase-to-voltage converter based upon differing phases of the voltage across the detector coil and the relationship between these phases and the position of the ferrite rod within the coil. Accordingly, the system may be used to accurately determine the position of the ferrite rod within the coil through measurement of phase changes across the detector coil.

(E) as is the case with the first described embodiment of the present invention, in the second embodiment thereof the position displacement sensor is totally electrically separated from the main electrical circuitry of the present invention and measurements of the position of the ferrite rod thereof within its respective coil are made through induced changes in the phase of a voltage across the detector coil of this embodiment. This feature quite significantly increases the flexibility of not only the second embodiment of the present invention but also of the first embodiment and enables either of these embodiments to be utilized in unusual situations where displacements of objects relative to one another are necessary such as for example two bones connected by a common joint in a human body.

Accordingly, it is a first object of the present invention to provide a displacement sensing device utilizing an adjustable tuned circuit.

It is a further object of the present invention that the displacement sensor thereof be unconnected to electrical circuitry forming a frequency generating as well as computing portion thereof.

It is a yet further object of the present invention to sense displacement by sensing a voltage drop on a source coil induced by a sensor coil capacitor combination arriving at its resonant frequency.

It is a still further object of the present invention to sense displacement by sensing phase changes in a voltage induced in a detector coil as a result of a sensor coil capacitor combination arriving at its resonant frequency.

It is a further object of the present invention to provide in the electrical circuitry a computer which controls the generation of sweeping frequencies provided to determine the resonant frequency of the sensing device and further provided for calculating the displacement corresponding to this frequency.

It is a yet further object of the present invention to provide electrical circuitry enabling the sensing of the displacements of a plurality of sensors in sequential fashion.

These and other objects, advantages and aspects of the present invention will be better understood from the following detailed description of the preferred embodiments when read in conjunction with the accompanying drawing figures.

BRIEF DESCRIPTION OF THE DRAWINGS

FIG. 15 shows a block diagram of the algorithm utilized in the system schematically shown in FIG. 2.

FIG. 16 shows a block diagram of the algorithm utilized in conjunction with the system schematically shown in FIG. 3.

SPECIFIC DESCRIPTION OF THE PREFERRED EMBODIMENTS

Theory

Figure 1:
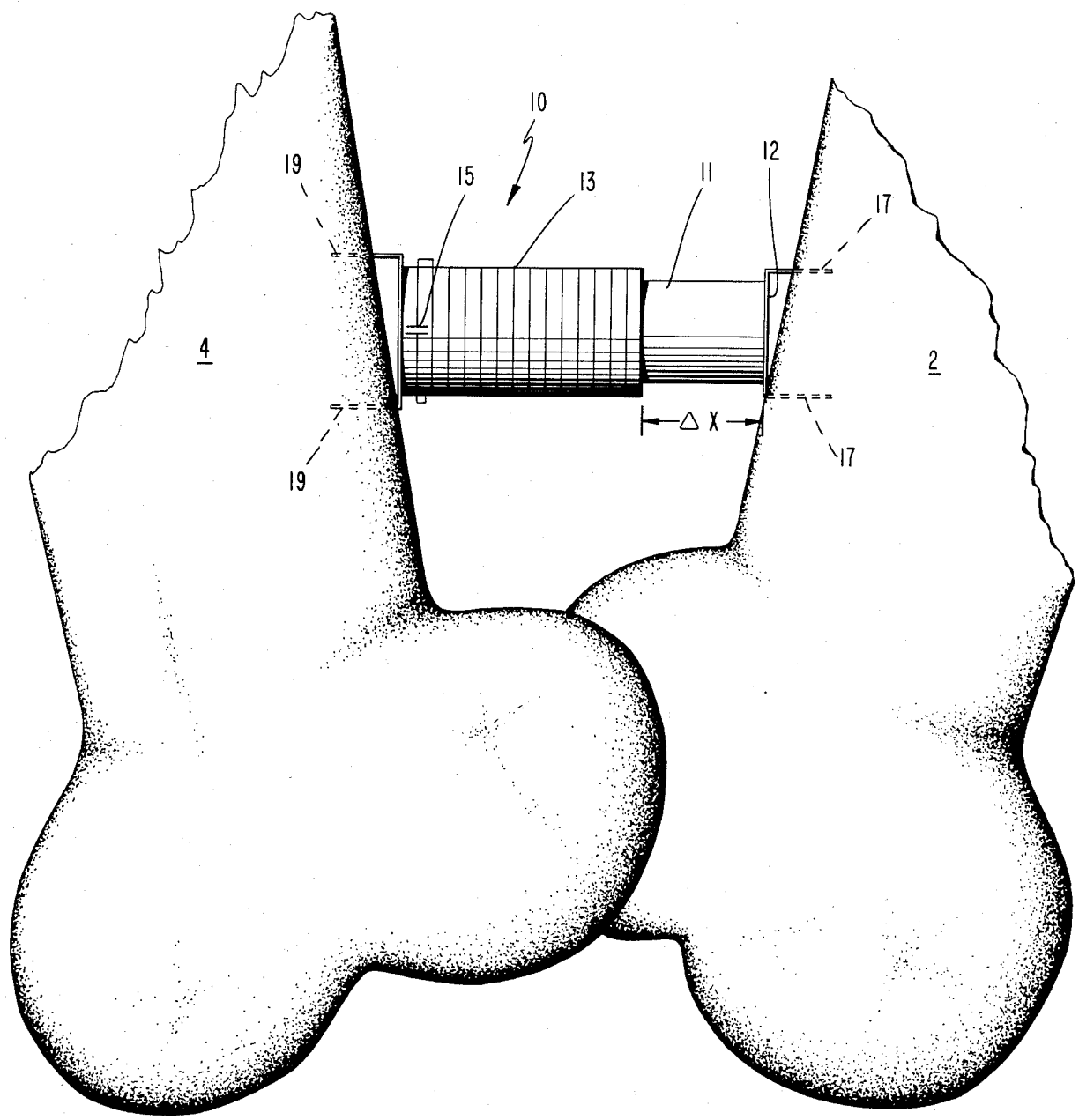
FIG. 1 shows a side view of the sensor of the present invention as attached to two bodies the relative displacement of which is to be determined.

Before specifically describing the preferred embodiments of the present invention, it is believed instructive to set forth the basic theories of operation of the present invention from which the preferred embodiments arise.

Voltage Amplitude Measurement

In the embodiment which relies upon voltage drop in the transmitter coil, the frequency of the transmitter is swept from $f_1$ to $f_2$ by applying voltage over a voltage-variable capacitor diode. A voltage will be induced over the sensor coil, at the sensor's resonant frequency $f_0$ which depends upon the position of the sensor ferrite rod in the sensor coil, which frequency $f_0$ is between $f_1$ and $f_2$. The induced energy in the resonant circuit will cause a dip in the voltage over the transmitter coil, when the transmitter is excited by a constant current source. The dip in voltage is equivalent to a conductance in parallel with the transmitter coil.

The induced voltage in the sensor coil is $$E_S = M_{TS} \cdot \frac{dI_T}{dt} = M_{TS} \frac{V_T}{L_T} \tag{1}$$

where
- $E_S$ = induced voltage in sensor coil
- $M_{TS}$ = mutual inductance (Transmitter-sensor)
- $I_T$ = current in transmitter coil
- $V_T$ = voltage over transmitter coil
- $L_T$ = inductance of transmitter circuit (coil)

The dip in the voltage over the transmitter coil is $$E_T = M_{TS} \frac{dI_s}{dt} = \frac{J\omega M^2_{TS} V_T}{L_T Z_S}, \tag{2}$$

where
- $E_T$ = induced voltage in the transmitter coil
- $I_S$ = current in sensor coil
- $J$ = is the base of the complex numbers $J^2 = -1$
- $\omega$ = radian frequency $\omega = 2\pi f$
- $Z_S$ = impedance of sensor circuit The current, that will run in the transmitter coil, due to this induced voltage is $$I'_T = \frac{E_T}{J\omega L_T} = \frac{M^2_{TS} V_T}{L_T^2 Z_S} \tag{3}$$

where
- $I'_T$ = current, that will run in transmitter coil, because of the induced voltage $E_T$ This is equivalent to a conductance in parallel with the transmitter coil $$G_T(\omega) = \frac{I'_T}{V_T} = \frac{Q_S K^2_{TS}}{\omega L_T} \left[ \frac{1}{1+x^2} - J \frac{x}{1+x^2} \right] \tag{4}$$

where $G'_T(\omega)$ = conductance in parallel with the transmitter coil (equivalent to the current $I'_T$)

$Q_S$ = quality factor of sensor, $\left( Q_S = \frac{\omega_o L_S}{R_S} \right)$ $R_S$ = resistance in sensor circuit $K_{TS}$ = transformer coupling coefficient $\left( K_{TS} = \frac{M_{TS}}{\sqrt{L_S L_T}} \right)$ $L_S$ = inductance of sensor circuit $X = 2 Q_S \frac{\omega - \omega_o}{\omega_o}$ -continued $\omega_o = 2\pi f_o$, where $f_o$ is the resonance frequency of the circuit.

The change in voltage over the transmitter coil is then $$V_T^i = V_T G_T^i(\omega) \frac{1}{G_T + G_T^i(\omega)} = V_T \left[ \frac{1}{\frac{1 + x^2}{Q_S Q_T K_{TS}^2} + 1} \right], \quad (5)$$

where $G_T^i(\omega)$ is the real part of $G_T(\omega)$, $x = 2Q_S \frac{\omega - \omega_o}{\omega_o}$, and $$\frac{1}{Z_S} = \frac{1}{R_S} \left[ \frac{1}{1 + x^2} - J \frac{x}{1 + x^2} \right].$$

Further, where
$V_T^i$=change in voltage over transmitter coil caused by the sensor
$V_T$=voltage over the transmitter coil, without any sensor present
$G_T = G_T^i = 1/Z_T$ conductance of transmitter circuit without any sensor present
$Q_T$=quality factor of the transmitter circuit without any sensor present.
$G_T(\omega) = G_T^i(\omega) + J\, G_T^{ii}(\omega)$ where $G_T^i(\omega)$ is the real part and $G_T^{ii}(\omega)$ is the complex part
$R_S$=resistance in sensor circuit A triangular voltage over the voltage-variable capacitor diode is used to sweep the frequency from $f_l$ to $f_2$ and back to $f_1$. The voltage over the transmitter coil is rectified and differentiated as a function of the frequency. The measured frequency corresponds to the zerocrossing of the differentiated voltage, $dV'_T/df$. This measurement is an average of a number of sweeps, where the part $dV_T/df$ will disappear, if $$\frac{dV_T^i}{df} >> \frac{DV_T}{df}.$$

Evaluation of the sensitivity parameters $$\frac{\partial S_\omega^V}{\partial K_{TS}}, \frac{\partial S_\omega^V}{\partial Q_T}, \text{ and } \frac{\partial S_\omega^V}{\partial Q_S},$$

where $$|S_\omega^V| = \left| \frac{\frac{\partial V_{TS}}{V_T}}{\frac{\partial \omega}{\omega_o}} \right|$$

and where $\frac{\partial S_\omega^V}{\partial K_{TS}}$ = the partial differentiation of $S_\omega^V$ by $K_{TS}$
The other ones are similarly defined.

$\phi TD$ = phase shift of the detector caused by the transmitted $\phi SD$ = phase shift of the detector caused by the sensor shows that $Q_S$ must be maximized and will have the most influence. The parameters $K_{TS}^2$ and $Q_T$ must also be maximized until $K_{TS}^2 Q_T G_T = 1$. It is better with a large $K_{TS}$ than a large $Q_T$, since a large $K_{TS}$ will make both the wanted signal and the noise sources larger.

Phase Measurement

The embodiment of the present invention using phase measurement consists of similar structure to the above described embodiment using amplitude measurements with an additional detector coil. The phase detection circuit is similar to the amplitude detection circuit, with the differences therebetween being specifically set forth hereinafter.

The phase of the detector coil is adjusted to 0° at the frequencies $f_1$ to $f_2$ without the sensor deployed. The frequency of the transmitter if swept from $f_1$ to $f_2$. The phase difference of the voltage induced from the transmitter coil and the induced voltage from the sensor coil is then measured at the detector coil.

The measured phase is converted to a voltage and the resonant frequency of the sensor is measured in a similar manner to the method described in amplitude measurement, with the measurement being the average of a number of sweeps. The part $$\frac{\partial \phi_{TD}}{\partial f}$$

will disappear, if $$\frac{\partial \phi_{SD}}{\partial f} >> \frac{\partial \phi_{TD}}{\partial f},$$

by using a triangular voltage over the voltage-variable capacitor diode to change the transmitter frequency.

The induced voltage, from the transmitter coil, in the detector coil is $$V_{TD} = M_{TD} \frac{dI_T}{dt} = K_{TD} \left( \frac{L_D}{L_T} \right)^{\frac{1}{2}} V_T. \quad (6)$$

where
$V_{TD}$=induced voltage in detector coil caused by the transmitter
$M_{TD}$=mutual inductance (transmitter-detector)
$I_T$=current in transmitter coil
$L_D$=inductance of detector circuit
$L_T$=inductance of transmitter circuit The induced voltage, from the sensor coil, in the detector coil is $$V_{SD}(\omega) = K_{TS} K_{SD} \left( \frac{L_D}{L_T} \right)^{\frac{1}{2}} Q_S V_T \left( \frac{x}{1 + x^2} + J \frac{1}{1 + x^2} \right), \quad (7)$$

where
$K_{TS} = M_{TS} (L_T L_S)^{-\frac{1}{2}}$, $K_{TD} = M_{TD} (L_T L_D)^{-\frac{1}{2}}$, and $K_{SD} = M_{SD} (L_S L_D)^{-\frac{1}{2}}$,
and where
$V_{SD}(\omega)$=induced voltage in the detector coil caused by the sensor as a function of $\omega$
$M_{TS}$=mutual inductance (transmitter-sensor)
$M_{TD}$=mutual inductance (transmitter-detector)
$M_{SD}$=mutual inductance (sensor-detector)

$K_{TS}$ = transformer coupling coefficient (transmitter-sensor)

$K_{TD}$ = transformer coupling coefficient (transmitter-detector)

$K_{SD}$ = transformer coupling coefficient (sensor-detector)

The measured phase in the detector coil is then $$\phi = \text{Arctan}\left(\frac{K_{TS} K_{DS} Q_S \frac{1}{1+x^2}}{K_{TD} + K_{TS} K_{DS} Q_S \frac{x}{1+x^2}}\right) \quad (8)$$

, where $\phi$ = measured phase in the detector coil

Evaluation of the sensitivity parameters $$\frac{\partial S_\omega^\phi}{\partial K_{TS}}, \frac{\partial S_\omega^\phi}{\partial K_{DS}}, \frac{\partial S_\omega^\phi}{\partial K_{TD}}, \text{ and } \frac{\partial S_\omega^\phi}{\partial Q_S},$$

where $|S_\omega^\phi| = \left|\frac{\frac{\partial \phi}{\partial \omega}}{\omega}\right|$ show. The parameter $K_{TD}$ should be zero and $Q_S$ should be maximized. The coupling coefficients $K_{TD}$ and $K_{DS}$ must be approximately 0.1% This will, with a reasonable voltage, say 5 volts, over the transmitter coil, get the voltage over the sensor and detector coils up in the mV range, far above the noise that is in the $\mu$V range Comparison In comparison of amplitude versus frequency techniques it can be seen from the respective sensitivity parameters, that if $Q_T = 1/K_{TD}$, the sensitivity will be the same. A large $Q_T$ will, however, increase the received signal from the noise sources. It is easier to create a small $K_{TD}$ than a large $Q_T$. Accordingly, the use of the phase measurement will therefore give a better sensitivity, but has the disadvantage that the phase measurement device must have one more coil than the amplitude measurement device.

Sensor

The sensor in each embodiment is a passive resonant circuit and consists of a coil and a capacitor. Changes in the capacitance $$\frac{dc}{dT}\Delta T$$

and in the inductance $$\frac{dL}{dT}\Delta T,$$

caused by temperature shifts, must be compensated for in order to avoid errors.

The frequency is, at $T_0$, $$f_0 = (LC)^{-\frac{1}{2}}, \quad (9)$$

and, at $T_1$, $$f_1 = \left(\left(L + \frac{dL}{dT}\Delta T\right)\left(C + \frac{dL}{dT}\Delta T\right)\right)^{-\frac{1}{2}}. \quad (10)$$

The following must be satisfied, in order to make $f_0 = f_1$ $$\frac{dL}{dT} C = \frac{dC}{dT} L, \quad (11)$$

and $$\frac{dL}{dT} \frac{dC}{dT} << \frac{LC}{(\Delta T)} \quad (12)$$

In equations 9–12,
L = inductance
C = capacitance
T = time
$\Delta T$ = increment of time Frequency The magnetic field is attentuated by propagating through the human body, when the system is utilized in an application including implantation of the sensor in the human body, for example at a bone joint. The skin-depth $\partial \cong 300 \, f^{-\frac{1}{2}}$ m for propagation through the body. This means that a frequency between 1 MHz and 10 MHz is a good choice. The signal is not attenuated too much and it is possible to achieve reasonable value for the quality factors Q of the coils.

Calculations have been made of: (1) the double induced voltage and (2) the sensor's influence on the frequency of the transmitter. It has been found that the errors will be less than 1% with proper design in accordance with the present invention.

Coils

The coil design parameters are N, I, L, $\mu_l$ and the dimensions of the coil. The size of the sensor coil is normally determined by the particular application thereof. The larger the value of $\mu_1$, the more magnetic field will be transmitted and/or received. Calculations show that $\mu_1 \geq 4$, if the sensor coil is limited to a cube dimension. By selecting a design where longer ferrite rods are possible, values for $\mu_l$ of greater than 20 may be achieved.

$\mu_o$ and $\mu_l$ are defined as follows:
$\mu_o = 4 \cdot 10^{-7}$ = permeability of free space
$\mu_l$ = relative permeability of coil The approximate inductance of a single layer air coil (which gives the best Q) may be calculated from the simplified formula:

$$L = 2.54 \frac{a^2 N^2}{9a + 10b} \, (\mu H), \quad (13)$$

where a is coil radius in cm, b is coil length in cm, and N is the number of coil turns. This formula is a close approximation for coils having a length equal to or greater than 0.8a.

The capacitance of the coil $C_1$ is about 10–20 pF and can be combined with the capacitance of the capacitor because the resistance of the capacitor $R_C$ is always very small.

It is known in the art that the spiral coil, used as transmitter coil, has a better sensitivity than a solenoid, but the calculations are more complicated. A spiral coil will be used as the transmitter coil in the embodiments of the present invention. The use of a spiral coil while advantageous from a sensitivity standpoint requires the inclusion of a special control circuit in order to obtain a constant voltage over the coil.

Measurements made in applicant's masters thesis entitled "Measurement of the Intercranial Pressure Using Inductive Coupled Coils", Technical University of Denmark, Lyngby, Denmark, January, 1976, show the following optimim dimensional criteria: (1) for the sensor: diameter $<0.5$ cm$\times$length$<2$ cm, $Q<100$, $N<100$, and $L<100$ $\mu$H, (2) for the transmitter coil: diameter $<20$ cm$\times$length$<2$ cm, $Q<100$, $N<10$, and $L<200$ $\mu$H. An accuracy better than 1% can be achieved through the use of sensor and transmitter coils made in accordance with the above criteria.

PREFERRED EMBODIMENTS

Now, with the theoretical aspects of the present invention having been set forth, specific descriptions of preferred embodiments in accordance with the present invention will now be described.

In each embodiment of the present invention, the sensor which is utilized will comprise that which is shown in FIG. 1. With reference to FIG. 1, the sensor 10 is seen to be connected between the bones 2 and 4. This is merely an example of an application of the present invention and, for example, the bones 2 and 4 could be adjacent vertebra or other bones connected adjacent one another or, if desired, any two objects whether within the human body or not the relative displacement of which is desired to be determined.

As shown in FIG. 1, the sensor 10 includes a ferrite rod 11, a coil 13 and capacitor 15 connected to the coil in parallel therewith. The coil 13 is so configured that the ferrite rod 11 may reciprocate within the coil 13. At one end of the sensor 10, a pair of hooks 17 are provided which enable attachment of the free end 12 of the ferrite rod to the first object, in this case the bone 2. On the other end of the sensor 10 adjacent one end of the coil 13 and the capacitor 15, a second set of hooks 19 is attached which enable the connection of this end of the sensor 10 to the other object, in this case the bone 4. As has been explained above, as the bones 2 and 4 pivot with respect to one another, with the respective hooks 17 and 19 attached thereto, the result is that the ferrite rod 11 will reciprocate with respect to the surrounding coil 13. This relative reciprocation will result in a relative change in the resonant frequency of sensor 10.

Figure 2:
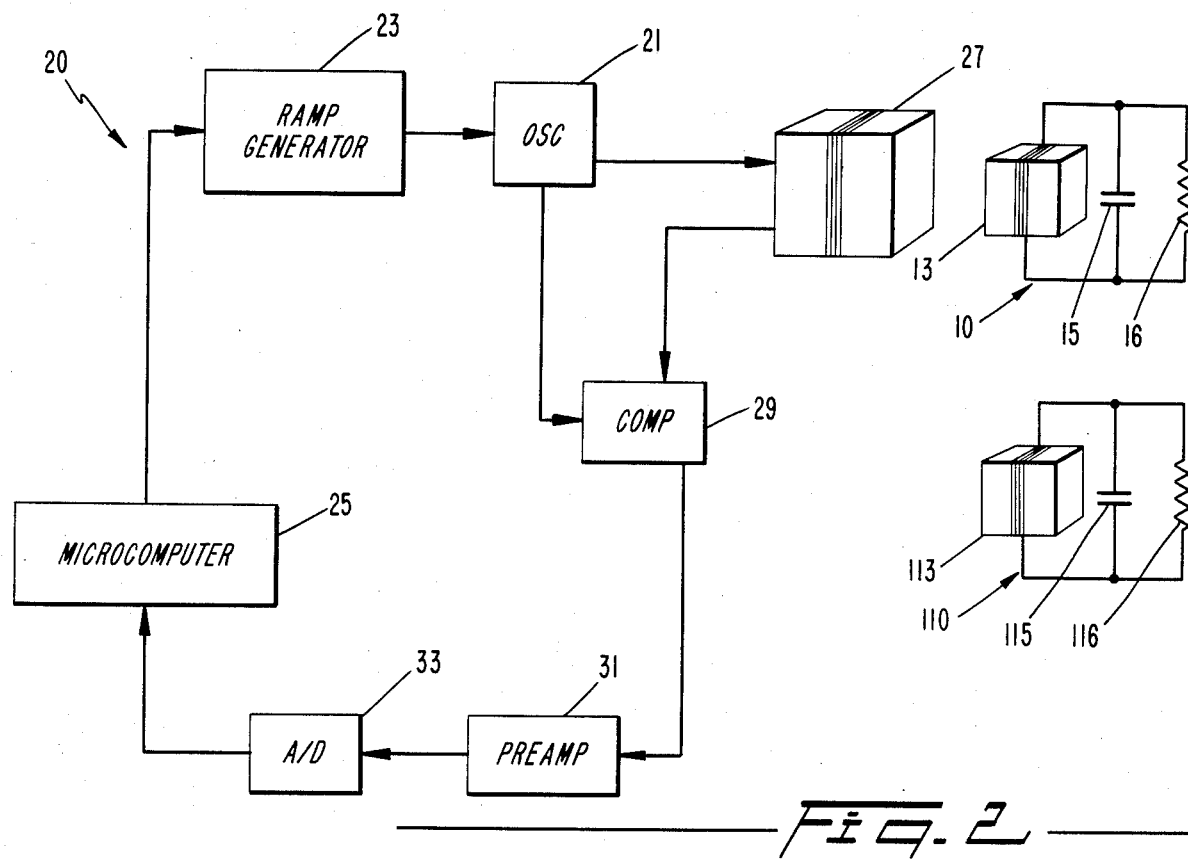
FIG. 2 shows a block diagram of a first embodiment of the present invention.

With this in mind, reference is now made to FIG. 2 wherein a block diagram of a first embodiment of the present invention is shown. As shown in FIG. 2, the first embodiment of the present invention designated by reference numeral 20 includes an oscillator 21 the frequency of which may be varied between known limits by applying the voltage from ramp generator 23 over a capacitance diode (not shown) within the oscillator. The microcomputer 25 controls all functions of the ramp generator 23 including its activation and deactivation. The oscillator 21 generates a voltage over the source coil 27 and thereby generates a magnetic field at the frequencies within which the oscillator 21 is operated. The sensor 10 is schematically shown in FIG. 2 and the specific structure thereof is shown in FIG. 1 as described hereinabove. It is noted, that in FIG. 2, the sensor 10 is seen to include a resistor 16. In reality, the sensor 10 does not include a resistor connected as shown in FIG. 2. The resistor 16 shown in FIG. 2 is indicative of the inherent resistances within the coil 13, capacitor 15 and the associated wiring within the sensor 10. Reference numeral 29 refers to a comparator which compares the difference between the voltage output of the oscillator 21 and the voltage output of the source coil 27. Any difference between these voltages is relayed to the preamp 31 which amplifies the difference signal and relays this amplified signal to the analog to digital converter 33 which converts the signal to a digital signal usable by the microcomputer 25.

As explained above, the position of the ferrite rod 11 with respect to the coil 13 varies as the two bodies 2 and 4 to which the respective ends of the sensor coil 10 are connected move with respect to one another. For each unique position of the ferrite rod 11 with respect to the coil 13, the sensor 10 will have a particular frequency at which it will resonate. The value in farads of the capacitor 15 and the range of values attainable by the coil 13 in henries are carefully chosen so that the resonant frequency of the sensor 10 will always be between the frequency limits of the oscillator 21. Since each attainable resonant frequency of the sensor 10 is precisely related to a position of the ferrite rod 11 within the coil 13, this data may be programmed into the microcomputer 25 so that the microcomputer 25 can output data indicative of the position of the ferrite rod 11 with respect to the coil 13. In further explanation, when the comparator 29 sends out a signal indicative of the fact that the voltage across the source coil 27 has dipped as a result of the oscillator 21 oscillating at the resonant frequency of the sensor 10, the microcomputer 25 knows at which frequency the source coil 27 suffered a voltage drop. As such, with knowledge of this information, the microcomputer may read out the position of the ferrite rod 11 with respect to the coil 13. Further, data may be programmed into the microcomputer 25 indicative of the position of the bodies 2 and 4 with respect to one another in the particular installation used.

FIG. 2 also shows a sensor 110 including coil 113, capacitor 115 and inherent resistance 116. The system 20 may be utilized to determine the resonant frequency of both sensors 10 and 110 since the sensor 10 is designed to resonate within a first range of frequencies and the sensor 110 is designed to resonate within a second range of frequencies which does not overlap the first range of frequencies. Thus the oscillator 21 may be swept through frequencies encompassing the first and second ranges to thereby enable determination of the resonant frequencies of the sensors 10 and 110. In a similar fashion as many sensors as desired may be simultaneously used.

Figure 3:
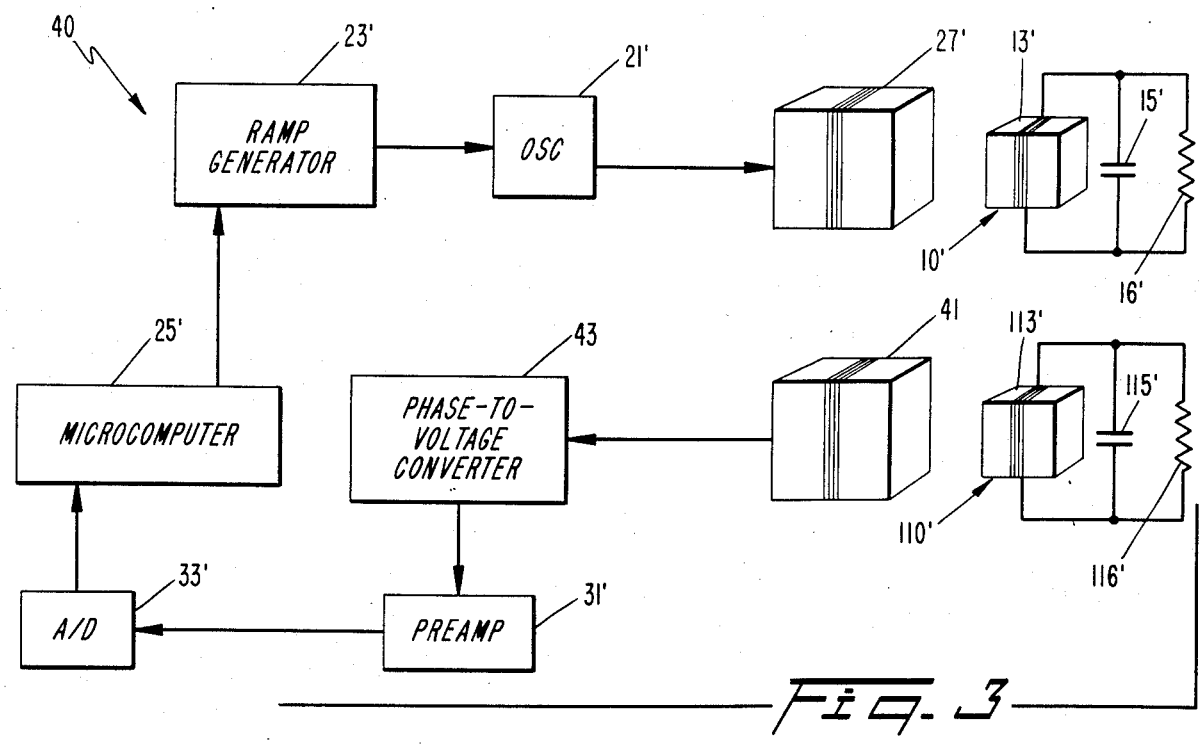
FIG. 3 shows a block diagram of a second embodiment of the present invention.

Referring now to FIG. 3, a second embodiment of the present invention will be described with like elements being referred to by like primed reference numerals. The system 40 shown in FIG. 3 includes an oscillator 21' powered by the ramp generator 23' so as to place an oscillating voltage across the source coil 27' which is adjusted by applying the voltage from the ramp generator 23' over a capacitance diode (not shown) in the oscillator 21'. The sensor 10' includes the coil 13' the capacitor 15' the inherent resistance 16' and the ferrite rod (not shown in FIG. 3). The system further includes a detector coil 41 which sends induced signals to a phase-to-voltage converter 43 which outputs voltages to a preamp 31' which amplifies the voltages and feeds them to an analog to digital converter 33' which converts the signals to signals usable by the microcomputer 25' in calculation of the position of the ferrite rod with respect to the coil 13'. In the operation of this embodiment, the frequency of the voltage across the source coil 27' is varied by the oscillator 21'. When this frequency is at the resonant frequency of the sensor 10', this fact is detectable through a change in phase of the voltage over the detector coil 41. This change in phase is converted to a voltage related thereto by the phase-to-voltage converter 43, which voltage is amplified in the preamplifier 31', converted to a digital signal in the analog-to-digital converter 33' and inputted into the microcomputer 25'. Since the computer knows at which frequency the phase change across the detector coil 41 was detected, this is the resonant frequency of the sensor 10', and the microcomputer is programmed with the various positions of the ferrite rod with respect to the coil 13' for each resonant frequency thereof. As such, from this information, the position of the bodies 2 and 4 with respect to one another may be determined.

FIG. 3 also shows a sensor 110' including coil 113', capacitor 115' and inherent resistant 116'. The system 40 may be utilized to determine the resonant frequency of both sensors 10' and 110' since the sensor 10' is designated to resonate within a first range of frequencies and the sensor 110' is designed to resonate within a second range of frequencies which does not overlap the first range of frequencies. Thus the oscillator 21' may be swept through frequencies encompassing the first and second ranges to thereby enable determination of the resonant frequencies of the sensors 10' and 110'. In a similar fashion, as many sensors as desired may be simultaneously used.

Signal Processing

Two preferred embodiments of the present invention having been described, it is believed instructive to go into further detail as to the signal processing thereof.

Figure 4:
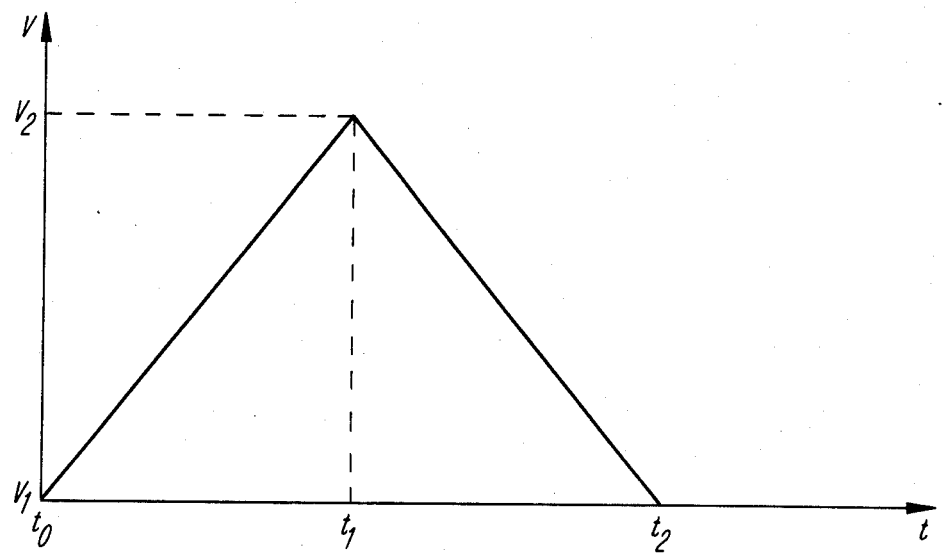
FIG. 4, shows a graph of ramp voltage as a function of time.

With regard to the embodiment of FIG. 2, the frequency of the magnetic field is varied from $f_1$ to $f_2$ and back to $f_1$ by applying a ramp voltage over a capacitance doide in the oscillator 21. FIG. 4 shows the ramp voltage as a function of the time. The ramp voltage changes the capacitance of the capacitance diode and thereby the frequency of the oscillator 21. The frequency of the magnetic field can be found from $$K_1 \frac{1}{\sqrt{LC}} \quad (1)$$

where $K_1$ is a constant.

Figure 5:
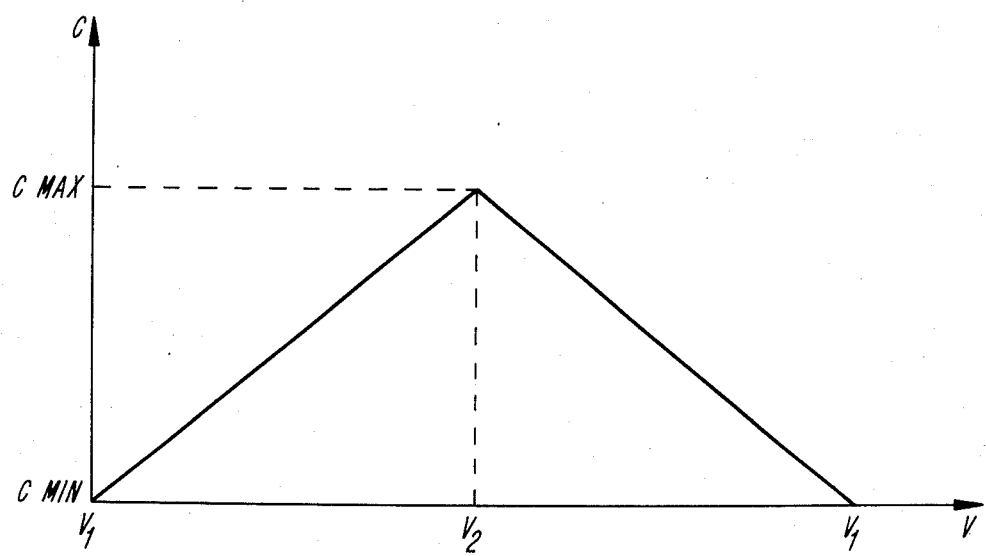
FIG. 5 shows a graph of capacitance of the capacitance diode of the oscillator as a function of the ramp voltage.
Figure 6:
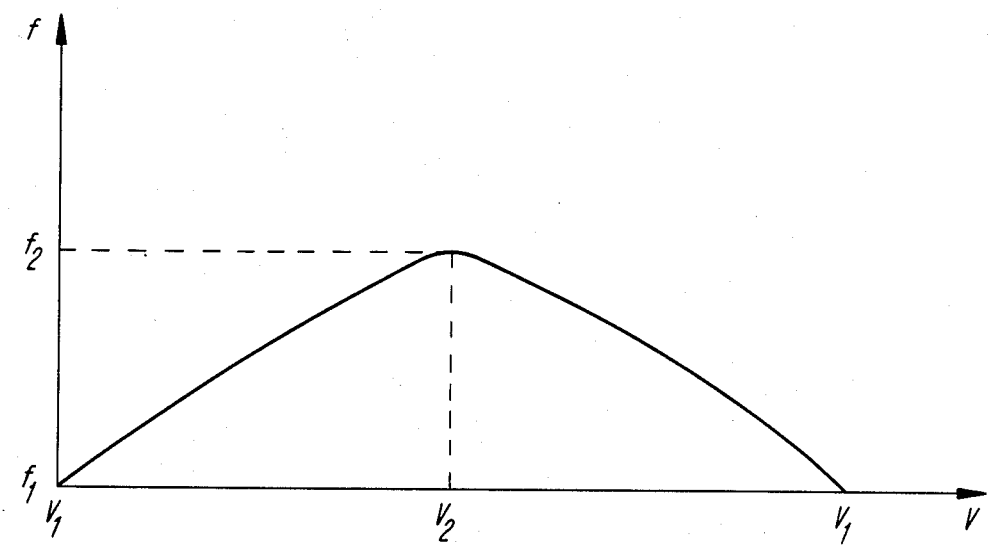
FIG. 6 shows a graph of the frequency of the magnetic field as a function of the ramp voltage.
Figure 7:
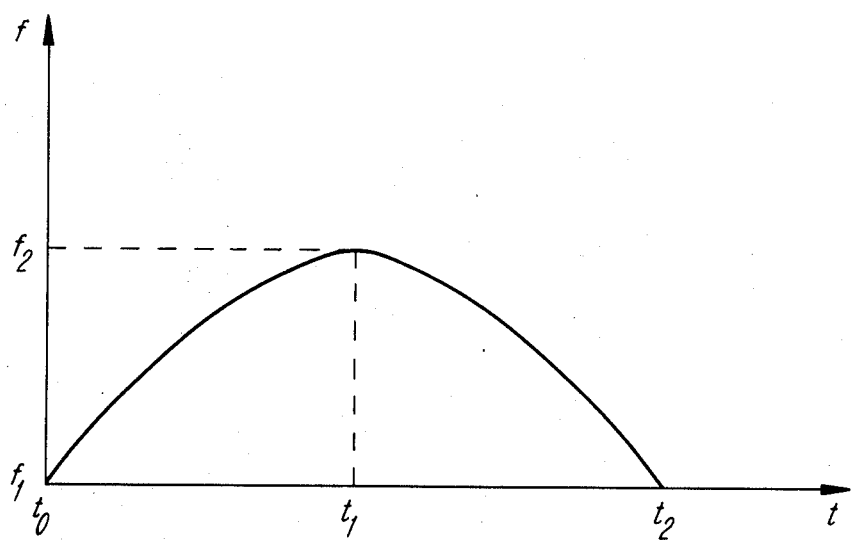
FIG. 7 shows a graph of the frequency of the magnetic field as a function of the time.

FIG. 5 shows the capacitance of the capacitance diode as a function of the ramp voltage. It is possible to find the frequency of the magnetic field as a function of the ramp voltage (See FIG. 6) from the functions shown in FIG. 4 and FIG. 5. It is also possible to find the frequency of the magnetic field as a function of the time (See FIG. 7 from the two functions shown in FIG. 4 and FIG. 6. The calculations are made in the microcomputer and the function shown in FIG. 7 is saved in the microcomputer memory for use in calculation of ferrite rod position.

Figure 8:
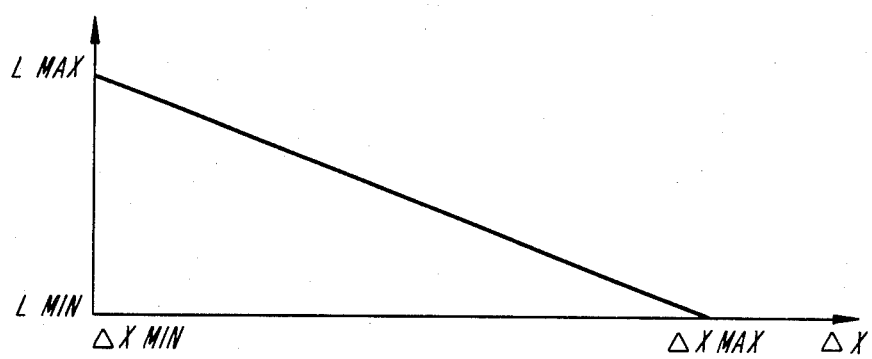
FIG. 8 shows a graph of the inductance of the sensor of FIG. 1 as a function of the movement of the ferrite rod thereof.

The movement (the displacement) of the body 2 relative to the body 4 (FIG. 1) will move the ferrite rod 11 in the sensor coil 13. The movement of the ferrite rod 11 in the sensor coil 13 changes the inductance in the resonance circuit comprising the sensor 10. FIG. 8 shows the inductance of the resonance circuit as a function of the movement of the ferrite rod 11 (the displacement $\Delta X$). The resonance frequency of the resonance circuit is varied, when the inductance is varied. The resonance frequency is found from $$K_2 \frac{1}{\sqrt{L_o C_o}} \quad (2)$$

where $K_2$ is a constant.

Figure 9:
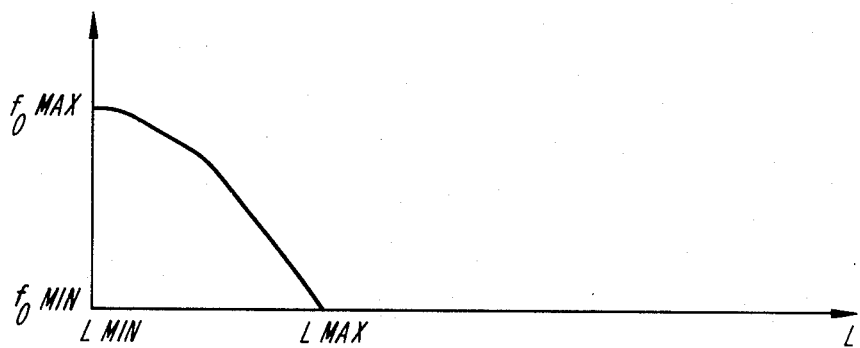
FIG. 9 shows a graph of the resonance frequency of the sensor shown in FIG. 1 as a function of the inductance thereof.
Figure 10:
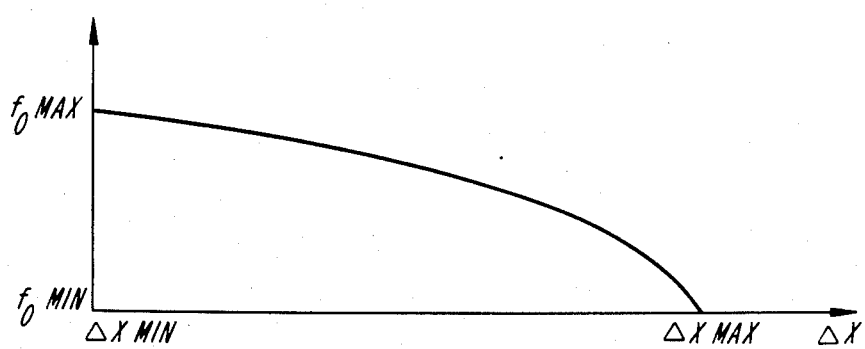
FIG. 10 shows a graph of the resonance frequency of the sensor shown in FIG. 1 as a function of the movement of the ferrite rod thereof.

FIG. 9 shows the resonance frequency as a function of the inductance L. It is possible to find the resonance frequency as a function of the displacement $\Delta X$ (See FIG. 10) from the two functions shown in FIG. 8 and FIG. 9. This is done in the microcomputer and the function is saved in the microcomputer memory for use in calculation of ferrite rod position.

Figure 11:
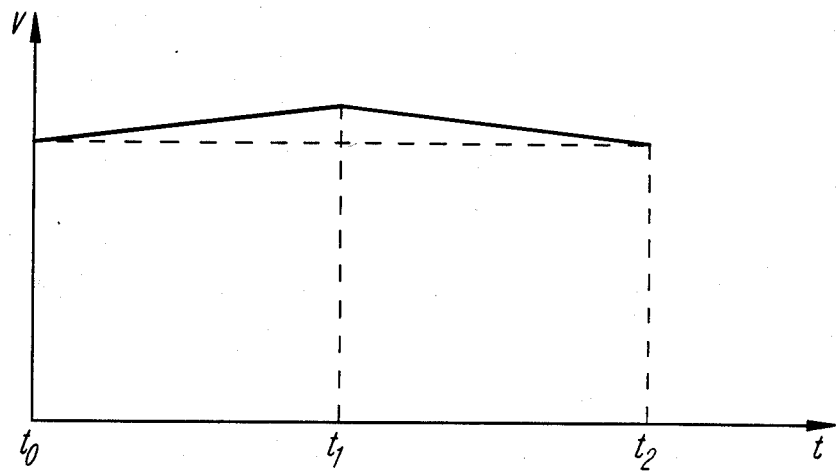
FIG. 11, shows a graph of the voltage over the source coil of the present invention as a function of the time without the sensor shown in FIG. 1 being adjacent thereto.
Figure 12:
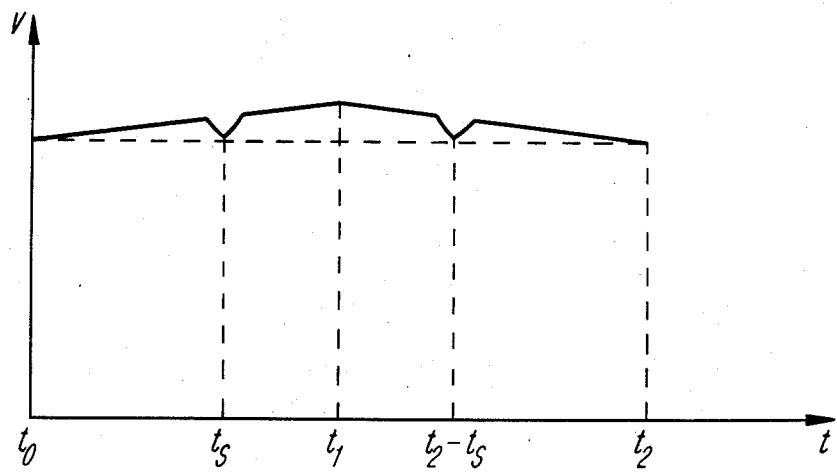
FIG. 12 shows the voltage over the source coil as a function of the time with the sensor adjacent to the source coil.

A voltage will be induced over the sensor coil, at the sensor's resonance frequency $f_o$, which is between $f_1$ and $f_2$. The induced energy in the resonance circuit will cause a dip in the voltage over the source coil, when the source coil is excited by a constant current source. FIG. 11 shows the voltage over the source coil 27, when the frequency is varied from $f_1$ and $f_2$ and back to $f_1$, without the sensor in place. FIG. 12 shows the voltage over the source coil 27, when the frequency is varied from $f_1$ to $f_2$ and back to $f_1$, with the sensor 10 in place. The curve in FIG. 12 shows two dips at the time $t_s$ and the time $t_2 - t_s$, both at the resonance circuit's resonance frequency $f_o$.

Figure 13:
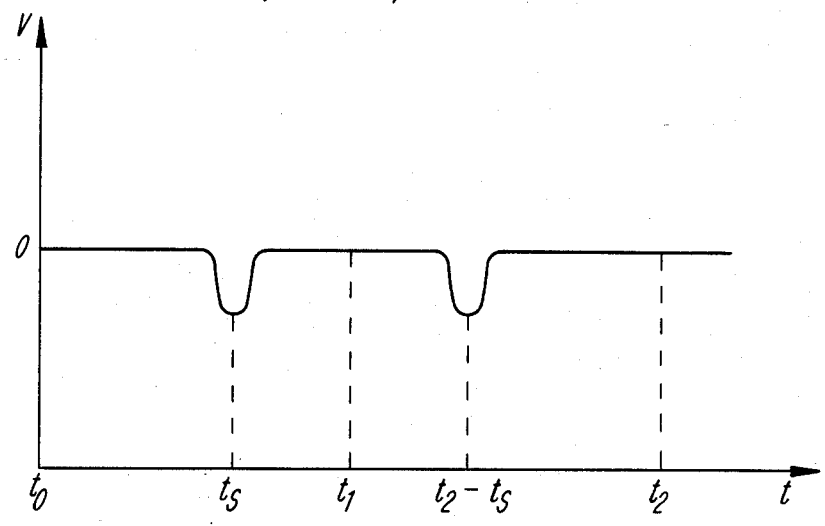
FIG. 13 shows a graph of the output from the comparator in the system of FIG. 2.

The voltage of the oscillator is subtracted in the comparator, and the resulting voltage, which is read into the microcomputer, is shown in FIG. 13.

The block diagram of the algorithm for the embodiment of FIG. 2 is shown in FIG. 15. The idea behind the algorithm is to find the time, $t_s$, for the instant when the maximum dip in the voltage over the source coil 27 occurs. The time $t_s$ is used to look up the frequency of the magnetic field (saved in the microcomputer memory as a function of the time $t_s$), FIG. 7. This frequency is the resonance frequency of the sensor 10. This frequency is then used to look up the displacement from the function, FIG. 10, of the resonance frequency as a function of the displacement $\Delta X$, which is stored in the microcomputer memory.

Figure 14:
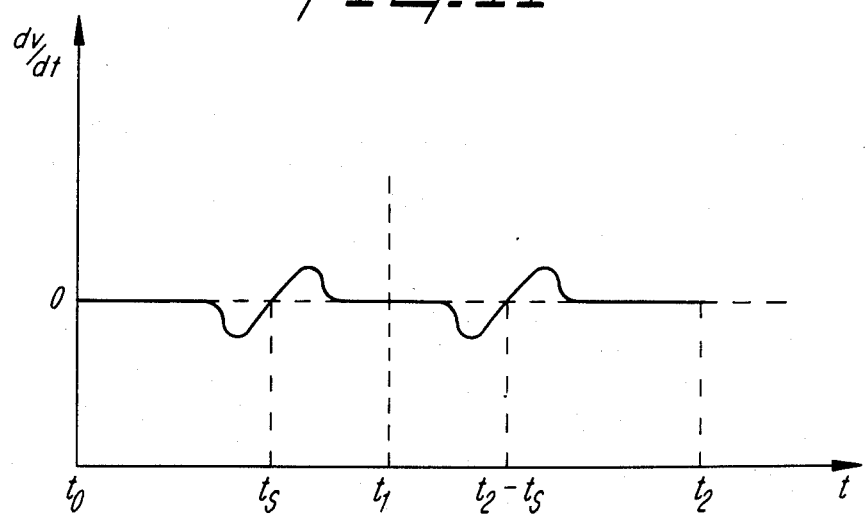
FIG. 14 shows a graph of the differentiated voltage over the source coil as a function of the time with the sensor in place.

The function shown in FIG. 14 is the output from the comparator 29 differentiated with the time as a function of the time. This differentiation is made in the microcomputer 25. This function is set equal to zero and the solution (the time, $t_s$) is that time when the sensor 10 is in resonance (when the dip in the voltage over the source coil 27 is at its maximum). This way of finding the time increases the accuracy in the determination of the time $t_s$. The frequency of the magnetic field is varied from $f_1$ to $f_2$ and back to $f_1$ in order to get two measurements of the time $t_s$, and thereby two calculations of the resonance frequency and the displacement, $\Delta X$. This gives easy comparison and enhanced accuracy. The accuracy of the determination of the resonance frequency is also enhanced, by varying the frequency of the magnetic field ($f_1$ to $f_2$) and then ($f_2$ to $f_1$).

The signal processing for the embodiment of FIG. 3 is similar to the signal processing for the first embodiment of the present invention. The block diagram for the algorithm is shown in FIG. 16.

The measured phase of the voltage over the detector coil 41 is changed, when the sensor 10' is in resonance. The maximum change occurs at the sensor's resonance frequency, $f_o$. The measured phase of the voltage over the detector coil 41 is converted into a voltage in a phase-to-voltage converter 43. This voltage is read into the microcomputer via the A/D converter 33'. This voltage is differentiated with the time as a function of the time. This function is set equal to zero and the solution $t_s$ is calculated. This time, $t_s$ is the time when the maximum phase change occurs, and is the time when the sensor 10' is in resonance. The sensor's resonance frequency is looked up in the saved function FIG. 7 (the frequency of the magnetic field as a function of the time) in the microcomputer 25'. This frequency is used to look up the displacement $\Delta X$ in the saved function FIG. 10 (the displacement $\Delta X$ as a function of the resonance frequency) in the microcomputer.

THE DISCLOSED SYSTEMS

The systems disclosed herein are displacement ($\Delta X$) measurement devices. They are primarily intended for the measurement of the displacement of one body 2 relative to a second body 4 inside a human or an animal body. The sensor 10 is implanted into a human or an animal body. The hooks 17 in the moveable ferrite rod are fastened to the body 2 and the hooks 19 in the sensor's base are fastened to the body 4. The detection system (the source), which measures the resonance frequency of the sensor and then calculates the displacement, $\Delta X$, is placed outside the human or the animal body.

The sensor 10 may be as small in size as 20 mm in length by 5 mm in diameter. The systems can measure the displacement of several bodies simultaneously, by using a sensor for each displacement. The measurement of the resonance frequencies of the different sensors and the calculations of the different displacements are made simultaneously.

The systems can also operate with the sensor not implanted into any human or animal body. The frequency of the system is preferably 1-10 MHz with an operation range of 100 mm if the sensor is implanted into a human body. The frequency and the operation range are different, if the sensor is not implanted. The frequency can be lower and the operation range longer, as desired.

The systems interface directly with any micro, mini, or mainframe computer via an A/D converter 33 and a digital in/output board.

The systems may also comprise a self-contained unit, with a microprocessor board, which may include the necessary EPROM and RAM memory, which do all the controlling and the calculations. The systems' analog parts interface directly to the microprocessor board via an A/D converter and a digital in/output board. The following applications for the systems disclosed herein exist, but the invention is not limited to these applications.

A. Implanted: The systems can easily be implanted in a human body or an animal body. They can be used to measure various displacements inside the body, such as the displacements of vertebrae, bones, ligaments, etc.

B. Gaitanalysis: The systems can measure the displacements of several targets simultaneously. They may be used for measurement of the angle of a bent arm, ankle, leg, knee, etc.

C. Robots: A robot utilizing a system in accordance with the present invention does not need to be pre-programmed. The objects that the robot is to operate on must have a target at the point where action is to be taken. The system enables dynamic interaction between the robot and the object.

D. Training: The systems can be used for training and education which require measurement of the displacement of any part of the body relative to a fixed point.

E. Games: The systems can be used as a displacement input device to be used in games.

While the preferred embodiments of this invention have been illustrated in the drawings and discussed in the hereinabove, it will be appreciated that variations and modifications of the present invention may be made without departing from the spirit and the scope thereof. Accordingly it is intended that the foregoing discription and drawings figures shall not be considered in a limiting sense but rather that the invention should only be limited by the scope of the following claims.

What is claimed is:

1. A method of monitoring the displacement of a first object with respect to a second object comprising the steps of:
   (a) attaching a sensor to said objects, said sensor including circuit means having a variable resonant frequency, said resonant frequency being varied by moving means in said sensor (1) attached to said objects and (2) moved in conjunction with movements of said objects with respect to one another;
   (b) measuring the resonant frequency of said sensor with measuring means unattached to said sensor;
   (c) calculating the relative position of said moving means; and
   (d) calculating the displacement of said first object with respect to said second object;
   (e) further wherein said sensor circuit means comprises:
      (1) capacitor means;
      (2) coil means connected in parallel with said capacitor means;
      (3) ferrite rod means located at least partially within said coil means;
      (4) said ferrite rod means being reciprocable with respect to said coil means, said coil means and ferrite rod means comprising said moving means.

2. The method of claim 1, wherein said attaching step includes the steps of:
   (a) attaching an end of said ferrite rod means remote from said coil means to one of said first object and second object;
   (b) attaching an end of said sensor remote from said end of said ferrite rod means to the other of said objects;
   (c) movement of said objects with respect to one another causing reciprocation of said ferrite rod means with respect to said coil means.

3. The method of claim 1, wherein said measuring step includes the steps of:
   (a) placing a voltage across a source coil with an oscillator;
   (b) sweeping the frequency of the oscillator voltage;
   (c) comparing the voltage output of the oscillator with the voltage output of the source coil;
   (d) from said comparing step, identifying at least one dip in said source coil voltage indicative of said source coil voltage having been oscillated at the resonant frequency of said sensor; and
   (e) determining said resonant frequency.

4. The method fo claim 1, wherein said measuring step includes the steps of (a) placing a voltage across a source coil with an oscillator;
(b) sweeping the frequency of said oscillator voltage;
(c) providing a detector coil;
(d) identifying at least one change in phase of voltage iduced in said detector coil by said sensor, said change in phase being indicative of said source coil voltage having been osciallted at the resonant frequency of said sensor;
(e) determining said resonant frequency;
(f) further wherein said identifying step includes the further steps of:
  (1) converting said phase changes to corresponding voltages; and
  (2) differentiating said corresponding voltages.

5. The method of claim 3, wherein said position calculating step further includes the steps of:
(a) storing data in a computer indicative of oscillator frequency as a function of time;
(b) storing data in said computer indicative of resonance frequency of said sensor as a function of the position of said ferrite rod means with respect to said sensor coil means;
(c) determining the time when said oscillator voltage frequency was at the resonance frequency of said sensor;
(d) retrieving data from said computer as to said resonance frequency from said time;
(e) inputting said resonance frequency into said computer, and
(f) retrieving data from said computer as to said position of said ferrite rod means with respect to said sensor coil means.

6. The method of claim 1, wherein said measuring step includes the steps of:
(a) placing a voltage across a source coil with an oscillator;
(b) sweeping the frequency of said oscillator voltage;
(c) providing a detector coil;
(d) identifying at least one change in phase of voltage induced in said detector coil by said sensor, said change in phase being indicative of said source coil voltage having been oscillated at the resonant frequency of said sensor;
(e) determining said resonant frequency.

7. The method of claim 6, wherein said position calculating step further includes the steps of:
(a) storing data in a computer indicative of oscillator frequency as a function of time;
(b) storing data in said computer indicative of resonance frequency of said sensor as a function of the position of said ferrite rod means with respect to said sensor coil means;
(c) determining the time when said phase change occured;
(d) retrieving data from said computer as to said resonance frequency from said time;
(e) inputting said resonance frequency into said computer, and
(f) retrieving data from said computer as to said position of said ferrite rod means with respect to said sensor coil means.

8. The mechod of claim 1, wherein the displacement of a third object with respect to a fourth object may be monitored by attachment of a further sensor therebetween having a variable resonant frequency within a range of frequencies different from the range of frequencies of the first recited sensor, the resonant frequency being varied by moving means and through the steps of:
(a) measuring the resonant frequency of said further sensor with said measuring means;
(b) calculating the relative position of said further sensor moving means; and
(c) calculating the displacement of said third object with respect to said fourth object.

9. A system for measuring the displacement of two relatively movable objects, comprising:
(a) sensor means connected between said objects, said sensor means including circuit means having a resonant frequency variable by relative movement of said objects; and
(b) electrical circuitry unattached to said sensor means for determining the resonant frequency of said sensor means and thereby the relative displacement of said objects comprising:
  (i) source coil means;
  (ii) oscillator means for placing a voltage across said source coil means;
  (iii) ramp generator means for controllably varying the frequency of said voltage in a sweeping manner; and
  (iv) controlling means for controlling the operation of said ramp generator, for determining the resonant frequency of said seonsor means and for calculating said displacement;
(c) further wherein said sensor means circuit means comprises:
  (1) capacitor means;
  (2) coil means connected in parallel with said capacitor means; and
  (3) ferrite rod means reciprocably mounted within said coil means;
  (4) reciprocation of said ferrite rod means with respect to said sensor means coil means altering the resonance frequency of said circuit means.

10. The system of claim 9, wherein said controlling means includes:
(a) computer means including a memory for storing data relating a range of resonance frequencies with respective said displacements; and
(b) analog-to-digital converter means for converting analog signals related to the particular resonance frequency of said sensor means into digital signals usable by said computer means to calculate said displacement.

11. The system of claim 10, wherein said controlling means further includes:
(a) comparator means for comparing the voltage of said oscillator means with the voltage of said source coil means;
(c) said comparator means outputting signals indicative of said dipping of said source coil means;
(d) said computer means receiving said comparator means signals and calculating therefrom said resonance frequency and said displacement.

12. The system of claim 10, wherein said controlling means further includes:
(a) detector coil means;
(b) phase-to-voltage converter means connected to said detector coil means;
(c) said sensor means inducing voltage across said detector coil means;
(d) said induced voltage undergoing change in phase at the resonance frequency of said sensor means;

(e) said change in phase being converted to a signal voltage related thereto by said phase-to-voltage converter;

(f) said signal voltage being inputted to said computer means via said analog to digital converter means;

(g) said computer means calculating from said signal voltage the resonance frequency of said sensor means and said displacement.

13. The system of any one of claims 11 or 12, including a plurality of sensor means, each sensor means connected to a respective pair of relatively movable objects, each sensor means resonating within a unique nonoverlapping range of frequencies said oscillator means being operable within a band of frequencies encompassing the entire range of frequencies of all of said sensor means.

14. A method of monitoring the displacement of a first object with respect to a second object comprising the steps of:

(a) attaching a sensor to said objects, said sensor including circuit means having a variable resonant frequency, said resonant frequency being varied by moving means in said sensor (1) attached to said object, and (2) moved in conjunction with movements of said objects with respect to one another;

(b) measuring the resonant frequency of said sensor with measuring means unattached to said sensor, said measuring means including excitation coil means for exciting said circuit means and detector coil means for detecting phase changes occurring at said resonant frequency;

(c) calculating the relative position of said moving means; and (d) calculating the displacement of said first object with respect to said second object.

15. The method of claim 14, wherein said measuring step includes the steps of:

(a) placing a voltage across a source coil with an oscillator;

(b) sweeping the frequency of said oscillator voltage;

(c) providing said detector coil means;

(d) identifying at least one change in phase of voltage induced in said detector coil means by said sensor, said change in phase being indicative of said source coil voltage having been osicallted at the resonant frequency of said sensor;

(e) determining said resonant frequency.

16. The method of claim 15, wherein said identifying step includes the further steps of:

(a) converting said phase changes to corresponding voltages; and (b) differentiating said corresponding voltages.

17. The method of claim 15, wherein said step of calculating the relative position of said moving means further includes the steps of:

(a) storing data in a computer indicative of oscillator frequency as a function of time;

(b) storing data in said computer indicative of resonant frequency of said sensor as a function of the position of a ferrite rod of said sensor with respect to a sensor coil of said sensor;

(c) determining the time when said change in phase occurred;

(d) retrieving data from said comptuer as to said resonant frequency from said time;

(e) inputting said resonant frequency into said computer; and (f) retrieving data from said computer as to said position of said ferrite rod with respect to said sensor coil.

18. A system for measuring the displacement of two relatively movable objects comprising:

(a) sensor means connected between said objects, said sensor means including circuit means having a resonant frequency variable by relative movement of said obejcts; and (b) electrical circuitry unattached to said sensor for determining the resonant frequency of said sensor means and thereby the relative displacement of said objects, comprising:

(i) source coil means;

(ii) oscillator means for placing a voltage across said source coil means;

(iii) ramp generator means for controllably varying the frequency of said voltage in a sweeping manner;

(iv) controlling means for controlling the operation of said ramp generator, for determining the resonant frequency of said sensor means and for calculating said displacement; and (v) said controlling means including detector coil means for detection of a maximum phase change which occurs at said resonant frequency.

* * * * *

UNITED STATES PATENT AND TRADEMARK OFFICE
CERTIFICATE OF CORRECTION

PATENT NO. : 4,618,822
DATED : October 21, 1986
INVENTOR(S) : Per K. Hansen

It is certified that error appears in the above-identified patent and that said Letters Patent is hereby corrected as shown below:

IN THE CLAIMS

Claim 4, line 8, (column 17, line 6),
  delete "iduced", insert --induced--.

Line 10, (column 17, line 8),
  delete "osciallted", insert --oscillated--.

Claim 8, line 1, (column 17, line 63),
  delete "mechod", insert --method--.

Claim 9, line 19, (column 18, line 27),
  delete "seonsor", insert --sensor--.

Claim 15, line 10, (column 19, line 45),
  delete "osicallted", insert --oscillated--.

Signed and Sealed this

Twentieth Day of January, 1987

*Attest:*

DONALD J. QUIGG

*Attesting Officer*  *Commissioner of Patents and Trademarks*